United States Patent
Paulson

(10) Patent No.: US 12,396,510 B2
(45) Date of Patent: Aug. 26, 2025

(54) BLACKBODY RADIATION SHIELD PROTECTIVE APPARATUS

(71) Applicant: PAULSON MANUFACTURING CORPORATION, Temecula, CA (US)

(72) Inventor: Roy Paulson, Murietta, CA (US)

(73) Assignee: Paulson Manufacturing Corporation, Temecula, CA (US)

( * ) Notice: Subject to any disclaimer, the term of this patent is extended or adjusted under 35 U.S.C. 154(b) by 1220 days.

(21) Appl. No.: 16/942,590

(22) Filed: Jul. 29, 2020

(65) Prior Publication Data

US 2020/0359729 A1    Nov. 19, 2020

Related U.S. Application Data

(63) Continuation of application No. 16/551,565, filed on Aug. 26, 2019, now abandoned, which is a continuation of application No. 15/993,248, filed on May 30, 2018, now abandoned.

(51) Int. Cl.
*A42B 3/20* (2006.01)
*A42B 3/28* (2006.01)

(52) U.S. Cl.
CPC . *A42B 3/20* (2013.01); *A42B 3/28* (2013.01)

(58) Field of Classification Search
CPC .......... A42B 3/20; A42B 3/28; F24F 2221/30; F24F 13/08; F24F 13/082
USPC ........................................................ 454/194
See application file for complete search history.

(56) References Cited

U.S. PATENT DOCUMENTS

| | | | |
|---|---|---|---|
| 1,400,860 A | 12/1921 | Brown |
| 1,995,456 A | 3/1935 | Kannel |
| 2,244,061 A | 6/1941 | Graves, Jr. |
| 2,354,466 A | 7/1944 | Levinsen |
| 2,579,942 A | 12/1951 | Thomas |
| 2,962,122 A | 11/1960 | Erik |
| 3,021,778 A | 2/1962 | Slatkovski |
| 3,139,503 A | 6/1964 | Latour |
| 3,270,171 A | 8/1966 | Latour |
| 3,348,466 A | 10/1967 | Lane |

(Continued)

FOREIGN PATENT DOCUMENTS

KR    101116947 B1    3/2012

OTHER PUBLICATIONS

U.S. Pat. No. 925144, A.J. Greenaway, issued Jun. 15, 1909.
U.S. Pat. No. 791773, A.D. Ward, issued Jun. 6, 1905.

*Primary Examiner* — Avinash A Savani
*Assistant Examiner* — Ryan L Faulkner
(74) *Attorney, Agent, or Firm* — Jaquez Land Greenhaus & McFarland, LLP; Bruce W. Greenhaus

(57) ABSTRACT

An arc flash protective hood device. The protective hood is fitted with a passive blackbody radiation shield device formed with facing plates, each plate having a plurality of slots therethrough, the slots in one plate being in offset registration with the slots in the other plate, thereby creating a semi-tortuous path for fluid flow through the device. The semi-tortuous path for air flow is so formed to prevent arc-flash energy from passing through the shield device. Alternatively, the shield device may be a single, integral element, or each plate may be made in two or more segments. The blackbody radiation shield device may be mounted in an opening in a hood, and several such shield devices may be mounted in several openings in the hood.

7 Claims, 14 Drawing Sheets

(56) References Cited

U.S. PATENT DOCUMENTS

| | | |
|---|---|---|
| 3,402,653 A | 9/1968 | Lex |
| 3,575,170 A | 4/1971 | Clark |
| 3,645,108 A | 2/1972 | Houk |
| 3,757,498 A | 9/1973 | Hurlbut, Sr. |
| 3,834,135 A | 9/1974 | Jordan |
| 4,356,012 A | 10/1982 | Hofstetter |
| 4,962,694 A | 10/1990 | Graver |
| 4,968,328 A | 11/1990 | Duke |
| 4,995,117 A | 2/1991 | Mirage |
| 5,212,843 A | 5/1993 | Kamata |
| 5,406,467 A | 4/1995 | Hashemi |
| 5,542,224 A | 8/1996 | Olsen |
| 5,758,639 A | 6/1998 | Konen |
| 6,019,421 A | 2/2000 | Roh |
| 6,176,239 B1 | 1/2001 | Grove |
| 6,290,742 B1 | 9/2001 | Pakkala |
| 6,302,785 B1 | 10/2001 | McKinney |
| 6,763,835 B1 | 7/2004 | Grove |
| 6,823,531 B1 | 11/2004 | Chen |
| 6,827,643 B2 | 12/2004 | Eiselt |
| 6,948,191 B2 | 9/2005 | Avery |
| 7,028,688 B1 * | 4/2006 | Grove .................... A62B 17/04 128/206.17 |
| 7,152,600 B2 * | 12/2006 | Freriks .................. A62B 17/04 128/205.27 |
| 7,178,932 B1 | 2/2007 | Buckman |
| 7,357,135 B2 | 4/2008 | Cunningham |
| 7,534,005 B1 | 5/2009 | Buckman |
| 7,585,345 B2 | 9/2009 | Smasal |
| 8,104,094 B2 | 1/2012 | Uttrachi |
| 9,372,004 B2 | 5/2016 | Sikkenga |
| 2005/0000199 A1 | 1/2005 | Carter |
| 2005/0136828 A1 | 6/2005 | Scasta |
| 2006/0273003 A1 | 12/2006 | Sudo |
| 2008/0127400 A1 | 6/2008 | Dupuis |
| 2009/0014005 A1 | 1/2009 | Mackinnon |
| 2010/0173206 A1 | 7/2010 | Wang Chen |
| 2011/0030114 A1 | 2/2011 | Merikoski |
| 2012/0086909 A1 | 4/2012 | Paulson |
| 2015/0072610 A1 | 3/2015 | Coles |
| 2015/0232796 A1 | 8/2015 | Martin |
| 2015/0362196 A1 | 12/2015 | Chen |
| 2016/0102455 A1 | 4/2016 | Burr |
| 2017/0079364 A1 | 3/2017 | Paulson |
| 2018/0104105 A1 | 4/2018 | Weirdert |
| 2019/0030382 A1 | 1/2019 | Roussos |

\* cited by examiner

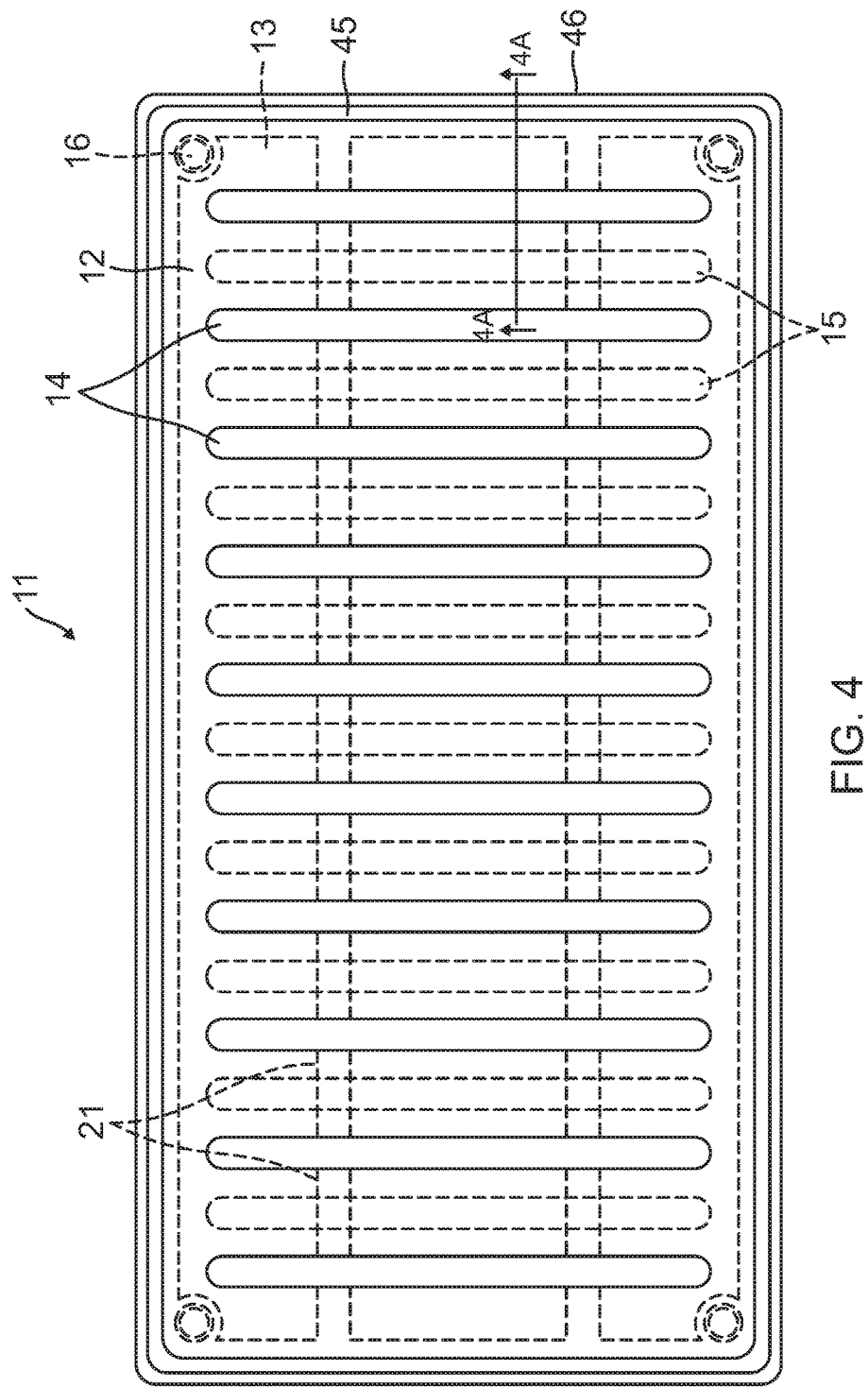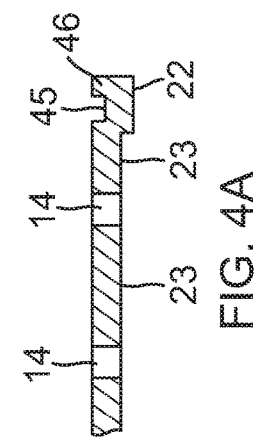
FIG. 4
FIG. 4A

BLACKBODY RADIATION SHIELD PROTECTIVE APPARATUS

FIELD OF INVENTION

The present apparatus relates generally to the field of personal protection equipment which protect people from life throating injury arising from electric-arc discharges and more particularly to a blackbody radiation shield which may be used together with safety helmets and face shields, for example.

BACKGROUND OF THE INVENTION

Electrical arc-flash hazards are a known threat in some workplaces and must be addressed to protect people who may be exposed t such dangerous conditions. Electric arcs or arc-flashes can result from short circuits developing from poor electrical grounding, failure of insulation, or workers inadvertently contacting exposed electrical circuit elements with objects such as tools. Electric arc-flashes have extremely high temperatures and near explosive power, and the energy they radiate can result in serious or fatal injury. The energy of an arc-flash is very intense and of very short duration. Flame resistant protective gear must be durable and able to withstand temperatures that may be as high as 35,000° F. To protect workers from exposure to such arc-flash events, a number of protective safety devices have been developed. In particular, face shields employing generally transparent windows comprised of compositions which have the ability for the user of the shield to see the workspace and, at the same time, have the ability to substantially block harmful radiation such as arc-flashes, are available. These devices are designed to provide protection against the thermal, optical, and mechanical hazards generated by arc-flash events. The known protective compositions are referred to as energy absorbing materials and are classified by their calorie ratings, that is, the level of energy for which they have been tested or certified.

When situational conditions or regulations so require, protective hoods are employed to protect the user's neck and upper shoulder area from arc-flash damage. Lack of adequate fluid, or air, flow is a typical consequence of the fact that hoods must be tightly sealed to the user's helmet, or face shield, or both, and envelop at least part of the user's upper body. Under typical working conditions, the upper body and head of the user, being closely confined, can become uncomfortably hot and humid, and subject to build-up of $CO_2$, due to inadequate provisions for air to easily exhaust from the hood. It has been difficult to exhaust fouled and heated air from such protective clothing because of the potential arc-flash energy that could penetrate the clothing through, openings intended to provide such air flow. Fan systems have been proposed with such hoods and have had some success. They would likely be battery powered. Fans are likely to add unwanted bulk, weight, and noise. Because of such wearing discomfort workers in dangerous areas where an arc-flash can occur may choose not to wear such protective hoods.

SUMMARY OF EMBODIMENTS OF THE INVENTION

A problem addressed by embodiments of this invention is to provide user with blackbody radiation shield protection in conditions where an arc-flash may occur, at the same time permitting air to flow out of the hood, thereby making the user more physically comfortable while working in such areas, with the gratifying knowledge that physical comfort has been measurably increased without degrading the level of protection afforded by the arc-flash protective apparatus. Knowing that arc-flash protection is maintained while physical comfort is increased enables a user to work at a high level of concentration to complete the job at hand quickly and efficiently.

An example of a purpose of the present concept is to maintain electromagnetic energy and infrared energy protection, a blackbody radiation shield device, while passively providing fluid flow for enhanced comfort of the user of protective fare shields with arc-protective clothing, such as hoods or shrouds, jackets, bibs, or suits. The term "hood" will be used herein as a convenient means to refer to all such arc-flash protective clothing, generally referred to as personal protective equipment (PPE), The term "fluid flow" is used herein as a more accurate term for the fouled air being exhausted from the hood, but "air" is not inaccurate.

A generally flat or planar fluid flow device or assembly is mounted in an opening in the hood. The mounting is sufficiently sealed so that the protective function of the hood is not compromised by installing one or more such fluid flow devices.

The fluid flow device itself is generally comprised of two spaced facing plates, an inner plate and an outer plate. Slots in the inner plate are in offset registration with slots in the outer plate, thereby providing fluid flow without degrading electromagnetic energy protection. The assembly of a paired inner plate with an outer plate may be mounted at any location, or more than one location, in a hood of the type that are typically employed in the field of protective clothing. The typical preferred location is at the back of the neck of the hood as worn by the user.

The term "offset registration" means that there is no direct pass-through route through the fluid flow blackbody radiation shield assembly and that air, for example, must move in a zig-zag, or semi-tortuous, path to pass from the inside to the outside, or vice versa. This offset registration results in electrical arc (arc-flash) radiation being blocked and thereby allowing flow of heated air from inside the hood while maintaining safety of the user from electric are energy. The fluid flow blackbody radiation shield device is passive, meaning that all parts are in fixed relation to all other parts. Offset registration may be obtained by the two facing plates having a different number of slots, for example, one having an even number and the other having an odd number. Alternatively, the slot numbers in the plates could be the same and the plates could simply be offset so that slots in one plate are faced by lands in the facing plate. The width of the respective, slots need not be all the same, but they must be arranged so there is no direct path through the slots in one plate to the slots in the second plate.

In an alternative embodiment, the fluid flow blackbody radiation shield device is formed of an outer plate having several parallel slots therethrough, and an inner baffle plate connected to and spaced from the outer slotted plate. The baffle plate is not formed with slots and it performs essentially the same function as the two facing plate embodiment having facing slots in offset registration.

While the device disclosed herein is particularly useful with arc-flash protective gear, it is also useful for any work environment when a hood is worn by the user for protection and heat builds up inside the hood.

BRIEF DESCRIPTION OF THE DRAWING

The purposes, features, and advantages of the disclosed structure will be more readily perceived from the following detailed description, when read in conjunction with the accompanying drawing, wherein:

FIG. 4 is a plan view of an embodiment of a fluid flow blackbody radiation shield device of this invention;

FIG. 4A is a partial sectional view taken along cutting plane 4A-4A of FIG. 4;

DETAILED DESCRIPTION OF THE PREFERRED EMBODIMENTS

Figure 2:
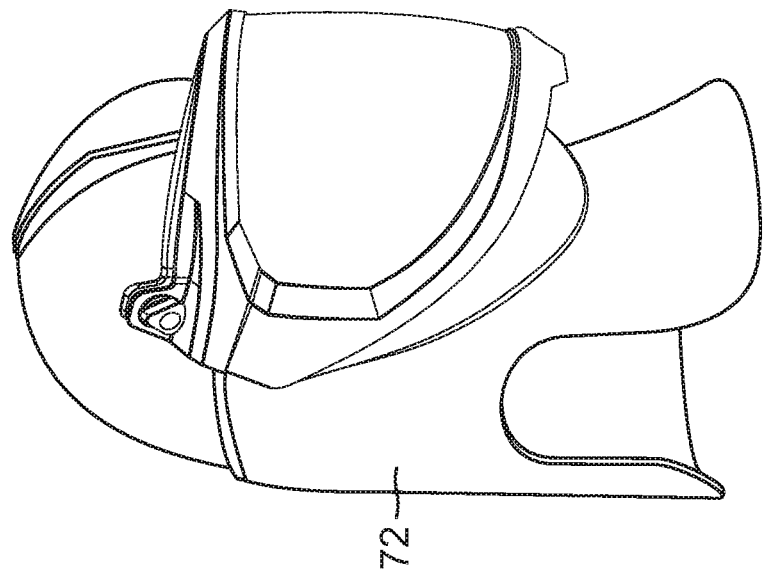
FIG. 2 is a perspective view of a shroud connected to a safety helmet and having a face shield of the prior art.
Figure 1:
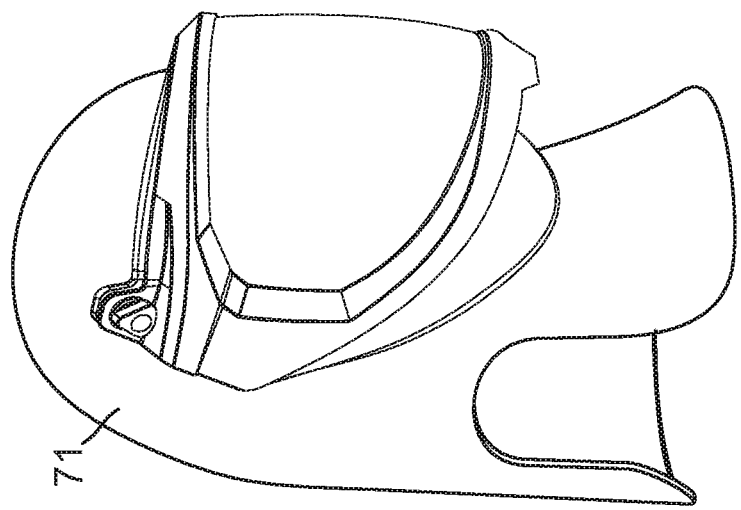
FIG. 1 is a perspective view of a protective hood with a face shield of the prior art.

For reference purposes, FIG. 1 shows a typical hood 71 and protective face shield, and FIG. 2 shows a typical shroud 72 connected to a safety helmet and having a protective face shield, either of which may be used together with the fluid flow blackbody radiation shield device described herein. The only significant difference between the shroud of FIG. 2 is that it is attached to a helmet, whereas the hood of FIG. 1 is not attached to a helmet and fits over the user's head, or course, a helmet should nor orally be worn by the user of the hood apparatus. Protective face shields are typically made of polycarbonate with additives of organic dyes or nanoparticles, or a combination of both. Suitable fabrics from which protective hoods may be made are available from commercial sources. Typical acceptable fabrics include WESTEX, a registered trademark of Milliken & Company, and PROTERA and NOMEX MHP, registered trademarks of E.I. du Pont de Nemours and Company.

Figure 3:
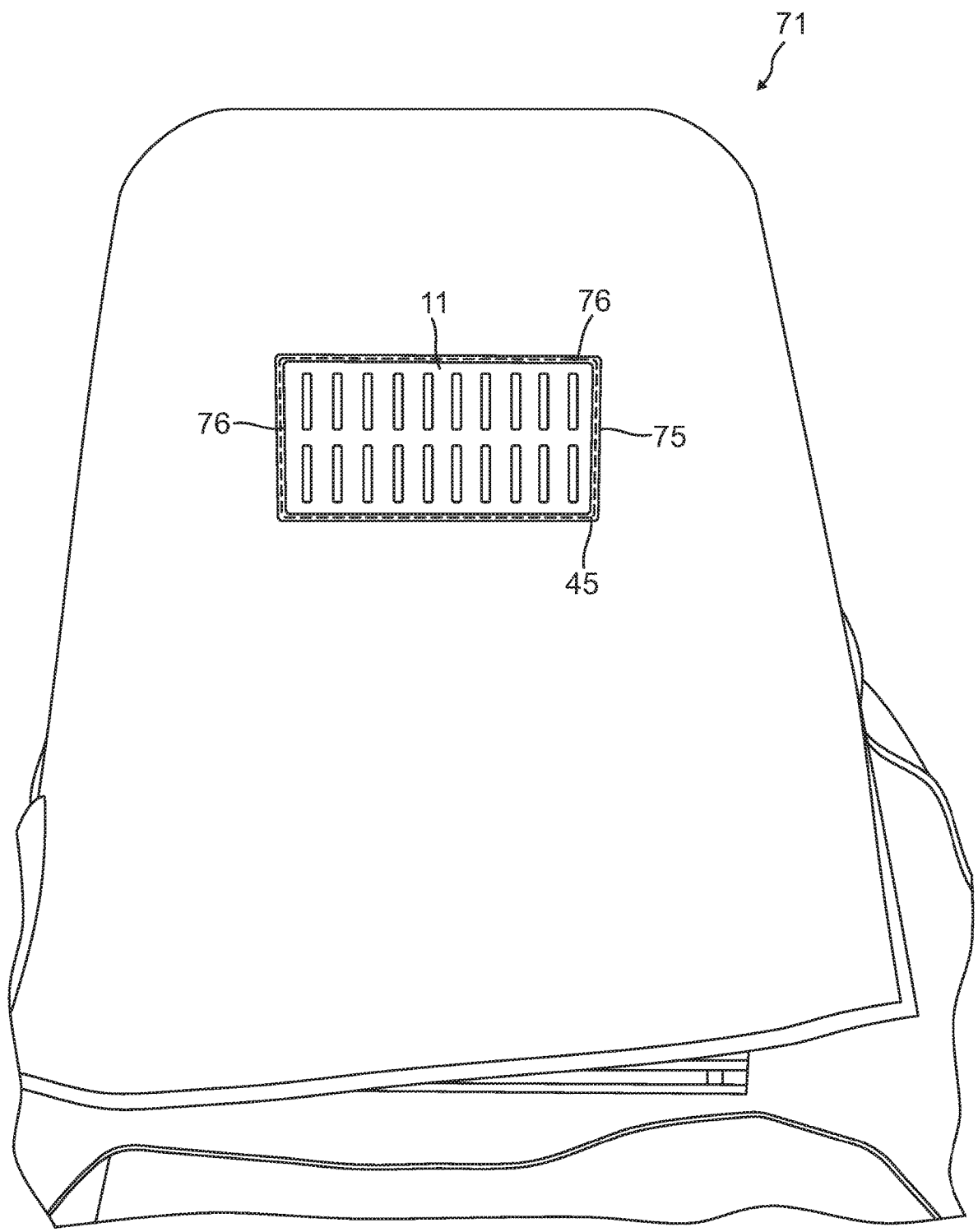
FIG. 3 is a somewhat schematic view of the back of a hood as it might appear with a fluid flow blackbody radiation shield device in accordance with embodiments of this invention mounted therein.

Given the situation when a worker is wearing a hood and protective face shield, as in FIGS. 1 and 2, plus, a helmet, and is working in a potentially dangerous arc-flash area, heat may quickly build up within the hood. The preferred location for fluid flow blackbody radiation shield device 11 in hood 71, 72 is at the back of the neck as shown in FIG. 3, where the hood fabric would normally not be in contact with the user's skin and air can flow relatively freely. In this position the heated and possibly otherwise fouled air can escape, clear of any work area. Any location from the back of the user's head to the shoulders or below could provide the desired fluid flow function.

To prepare the hood to receive radiation shield device 11, a rectangular opening 76 is made in the hood in the area that would be at the back of the user's neck or in that general vicinity, and the unitary or assembled device 11 (described in detail herein) is secured in the opening by suitable means. While it could be secured by an appropriate adhesive, for example, the preferred method is to stitch the device to the hood with appropriate fire-retardant thread material 75 in groove 45 (see FIG. 3A). Stitches of thread 75 can be seen in FIG. 3. Examples of materials from which thread 75 can be made include fiberglass, and KEVLAR and NOMEX, both registered trademarks of E.I. du Pont de Nemours and Company for synthetic fibers and fabrics made from those fibers.

Figure 3A:
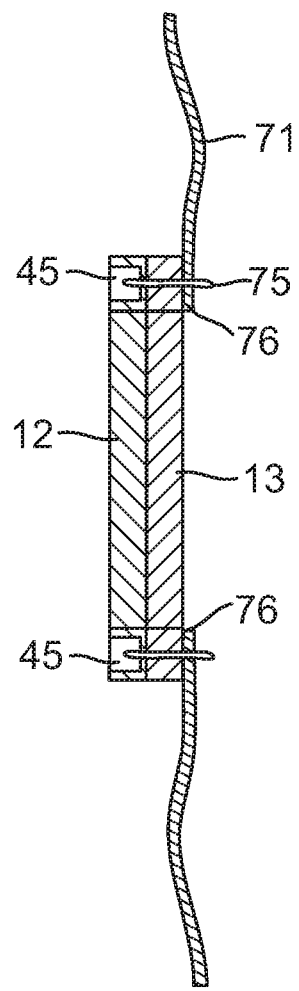
FIG. 3A is a partial sectional view of the fluid flow blackbody radiation shield device and hood fabric of FIG. 3.

As can be seen in FIG. 3A, opening 76 in hood 71 is peripherally smaller than is radiation shield device 11, enabling stitches 75 to positively secure the device in the opening.

Figure 5:
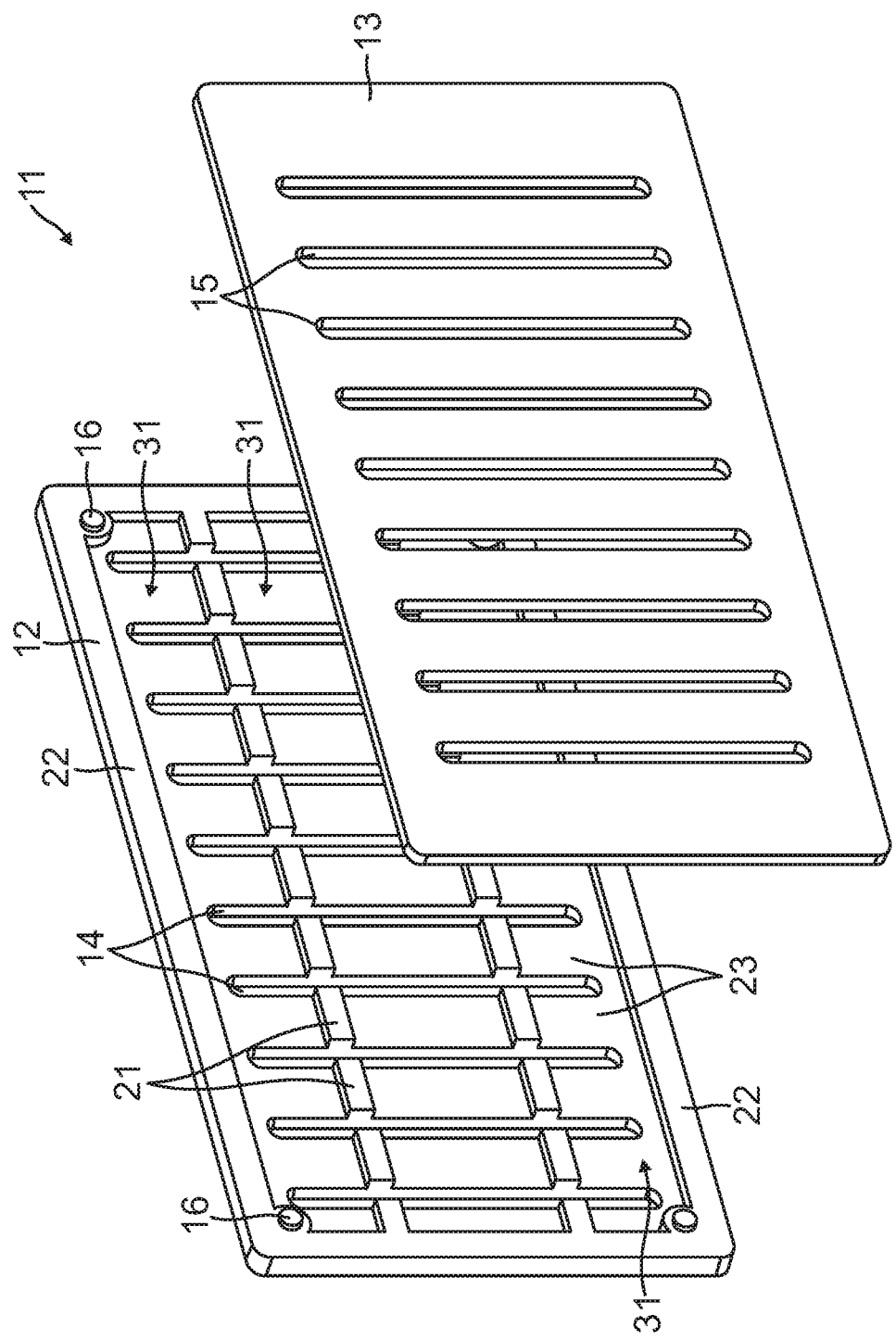
FIG. 5 is an exploded perspective view of the device of FIG. 4 from one side.
Figure 6:
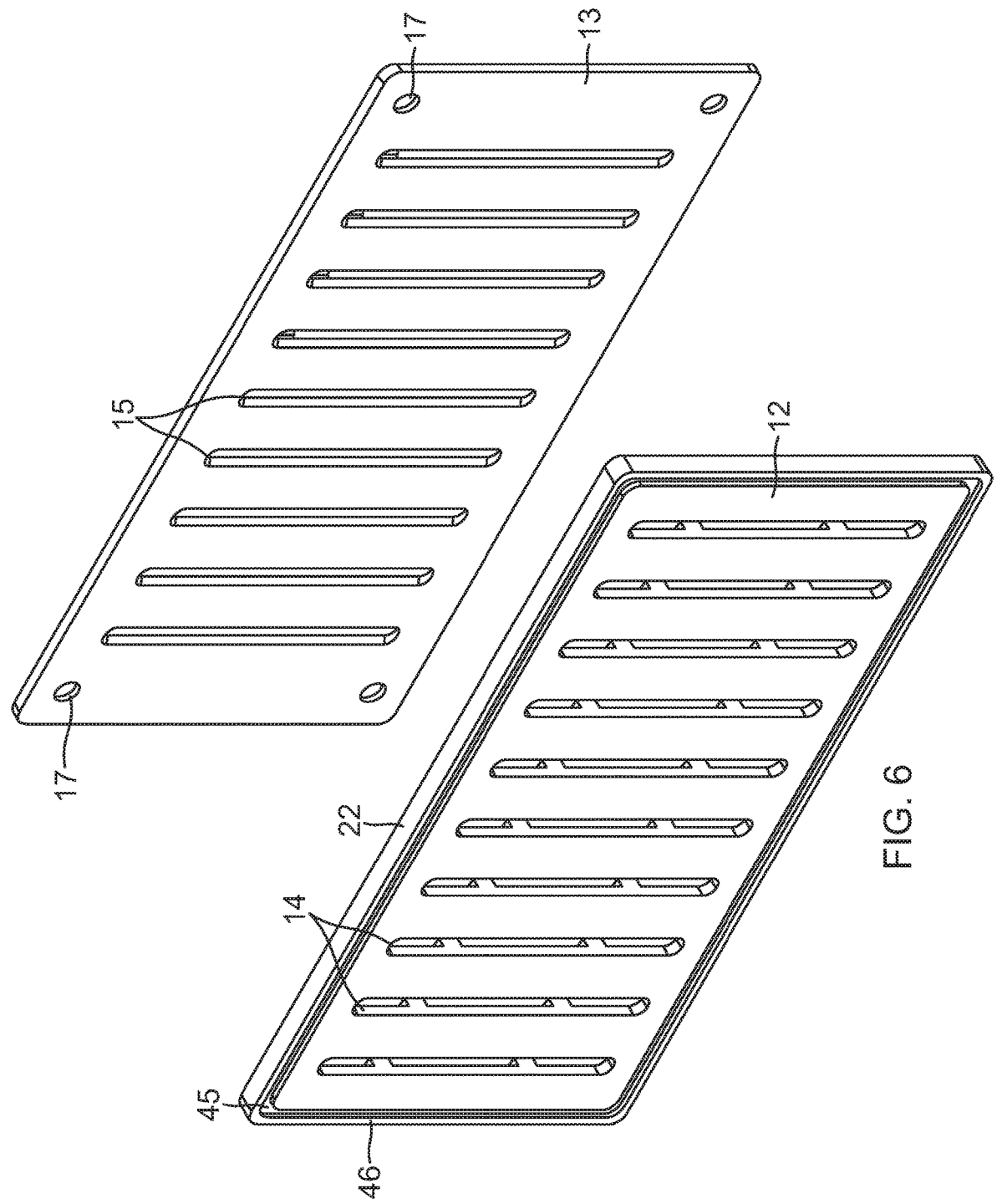
FIG. 6 is an exploded perspective view of the device of FIG. 4 from the opposite side.

With reference now to FIGS. 4-6, passive fluid flow blackbody radiation shield device 11 is preferably comprised of front, or first, plate 12 mounted to back, or second, plate 13. The terms "front" plate and "back" plate, or "first plate" and "second plate," are used for convenience only and are not intended to designate a particular one of those plates to be outside or inside with respect to the clothing items to which the device is intended to be mounted. Either, or both plates, could be made of more than one plate or as a unitary plate, as is deemed practical and appropriate for the purpose for which it is intended to be used. As further alternatives, the entire device 11 could be formed as a unitary product, which could be injection molded, 3-D printed, or made by some other process.

For purposes of this description, front and back plates 12 and 13 and device will be discussed as having the parameters set, forth below, no matter how the device is formed or assembled.

Plate 12 is formed with a plurality of parallel slots 14 therethrough. Plate 13 is formed with a plurality of parallel slots 15 therethrough. As shown, there are ten slots in plate 12 and nine slots in plate 13. There is no requirement that the number of slots be any particular number, only that they be offset with respect to each other when the plates are assembled in face-to-face relationship. Also, the number of slots through plate 12 may be the same as the number of slots in plate 13. They still would be of set to create a semi-tortuous path for fluid flow therethrough. That structural requirement will be discussed further below.

Plate 12 is shown formed with registration pins 16 near the periphery of each corner. Plate 13 is formed with similarly positioned matching holes 17. These may be blind holes or through holes. Holes 17 are configured to match with pins 16 so that plates 12 and 13 can be secured together in fixed registration relationship. It is preferred that plates 12 and 13 be secured together to form a unitary device, as shown in FIG. 4.

The side of plate 12 facing plate 13 is formed with stand-offs 21 which contact the inside surface of plate 13 and maintain fluid flow spaces 31 between the plates. As shown in FIG. 5, rim 22 and stand-offs 21 are all of the same thickness. As an alternative way of saying it, the rim and the stand-offs are in the same plane on the side of plate 12 facing plate 13. The remaining portion of the inside surface of plate 12, including lands 23, is depressed, or thinner than are rim 22 and stand-offs 21, thereby forming lateral air flow spaces 31.

As can be seen in FIG. 4, when holes 17 in plate 13 are in registration with pins 16 in plate 12 and the two plates are mounted together, slots 14 and 15 are in offset registration, as previously stated. Air can flow in through slots 14, pass laterally in, spaces 31 between the plates for a short distance between the inside surface of plate 13 and lands 23, and flow out through slots 15 in plate 13 in a semi-tortuous manner. Of course, flow could just as well be in the opposite direction. Because plate 13 is planar and rim 22 and stand-offs 21 are co-planar, air is generally confined to spaces 31 for lateral movement. However, it is not necessary that plates 12 and 13 be sealed together, but they would generally be secured together and the inside surface of plate 13 would be in contacting relation with rim 22 and stand-offs 21.

The spaces 31 between the inside surface of plate 13 and lands 23 of plate 12, in relation to the width of the slots, should be just enough to prevent any unimpeded fluid flow and, at the same time block arc-flash or radiation energy through device 11. One test to ensure that arc energy cannot pass directly through device 11 is to view the device normal to the slots and at a 45° angle from above the device. If there is no direct visibility through device 11 from that 45° angle position, there would be no penetration of arc-flash energy therethrough. Stated another way, spaces 31 needs to be only sufficiently separated from the inside surface plate 13 to permit lateral fluid flow between plates 12 and 13 within the spaces 31.

Device 11 may be formed of known blackbody radiation, arc-flash, or arc-energy resistant, blocking, or absorbing material, such as rubber or a thermoplastic, having the same calorie rating as would a face protective shield or window and the hood used with the window. There may be several formulations of the constituents of which plates 12 and 13 are formed. Device 11 must be electrically non-conductive and it could be rated as dielectric. Any materials which meet the protective, energy absorbing requirements of the hood fabric and the protective window, would normally be acceptable for these device plates.

Device 11 may be made from a thermoplastic elastomers or thermoplastic vulcanizate such as SANTOPRENE, a registered trademark of Exxon Mobil Corporation. Alternative materials from which device 11 can be formed include EPDM rubber, silicone rubber, or neoprene rubber. There may be other high temperature resistant materials that are acceptable. As a further example, carbon black may be added to SANTOPRENE to result in an arc-energy blocking device. Other materials that are tuned to the electromagnetic spectrum of an arc-flash (200-3000 nm as an example), include organic dyes, nanoclays, and nanoparticles.

The structure of device 11 ensures that there is no direct, unimpeded thud flow route from one side to the other, so the user is protected from potential arc flash injury, which is a direct blast onto the surface of device 11. At the same time, air can flow through device 11 as previously described, providing much needed relief for the user from the build up of hot, fouled atmosphere within the protective covering when wearing a hood equipped with device 11.

Plate 12 is formed with narrow peripheral groove 45 (FIGS. 4, 6, and 7) in rim 22, just inside edge 46. This is used in securing device 11 to clothing, as will be discussed below. This is shown clearly in the cross-sectional view of FIG. 4A.

Figure 7:
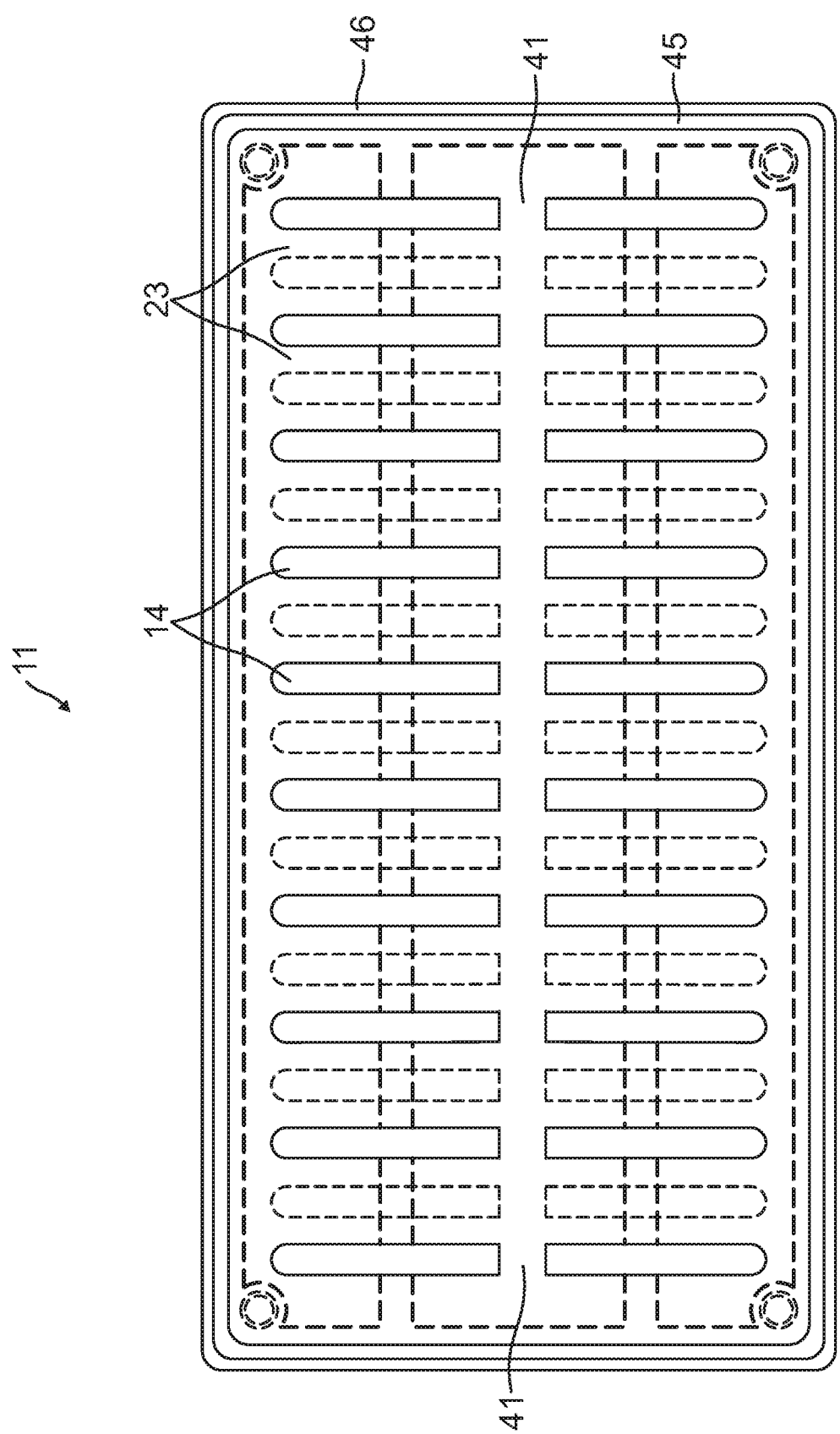
FIG. 7 is a plan view, similar to FIG. 4, of an alternative embodiment of a fluid flow blackbody radiation shield device of this invention.
Figure 8:
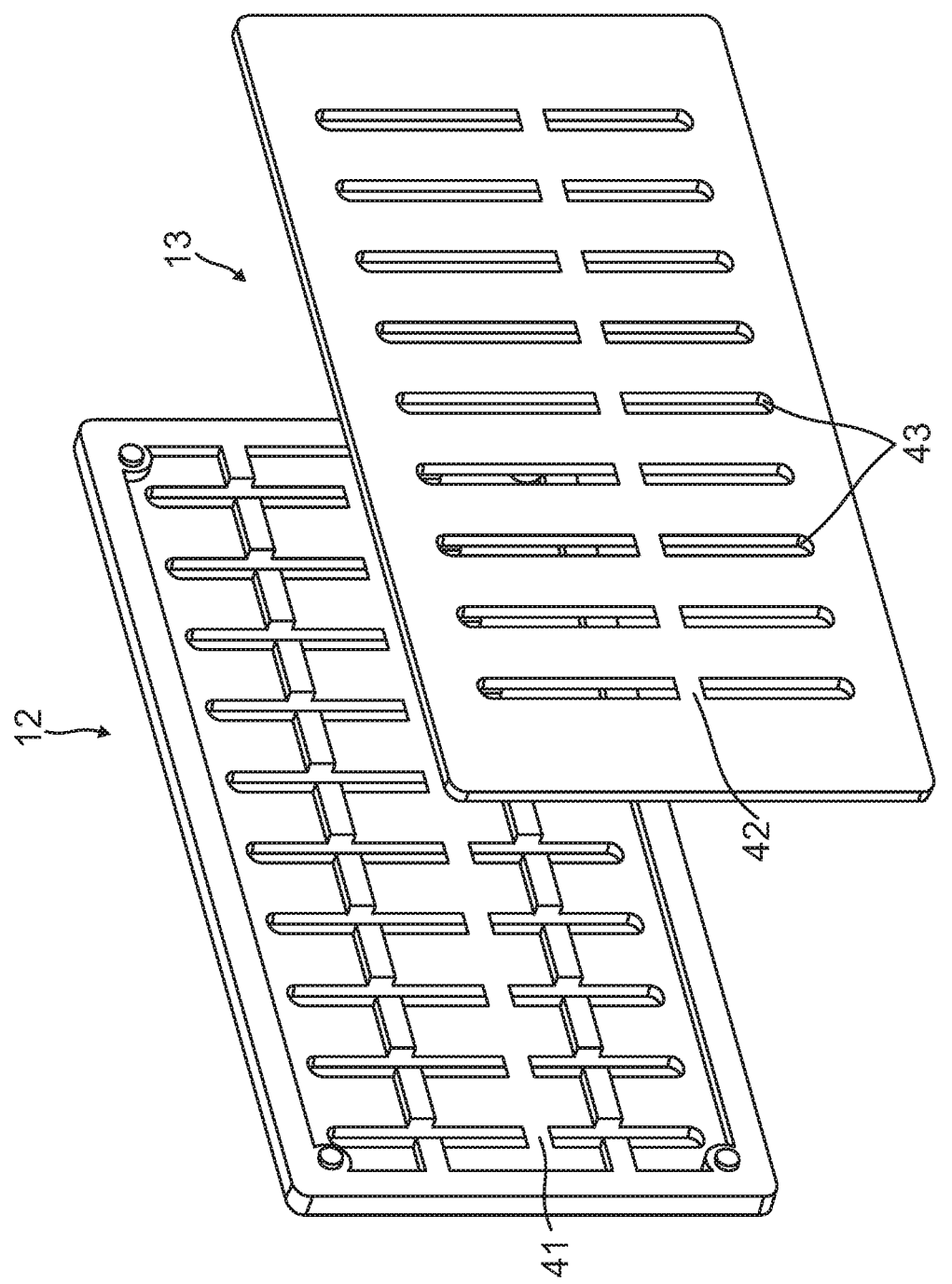
FIG. 8 is an exploded perspective view of the device of FIG. 7.

An alternative embodiment of device 11 is shown in FIGS. 7 and 8. Device 11 may be relatively rigid. When the device is made of materials which are somewhat flexible, such as rubber, it has been found that bridges 41 help maintain stability of lands 23 and, consequently, of slots 14 with respect to each other in plate 12. Similarly, bridges 42 span slots 43 in plate 13 for the same purpose. Each plate 12, 13 then effectively has the form of two coplanar segments separated by bridges 41, 42, respectively.

By the terms "relatively rigid" and "somewhat flexible" it is meant that device 11 is firm, as is a rubber plate, and that it is not readily flexible, as is flexible clothing, that is, hood 71, for example. Device 11 is made from a rubber-like material having a flex modulus that allows the material (device 11) to bend to conform to the fabric of hood 71 and has a low elasticity that keeps the device from distorting, thereby preventing arc-flash energy from passing through the offset slots. As a readily understood and visualized analog, a slab or bar of rubber cut from an automobile tire would be an example of relevant stiffness with some flexibility but is not "rigid."

FIGS. 9A-E shows examples of possible shapes of device 11 in addition to the rectangular shape of FIG. 4. Each would include the same characteristics as the devices of FIGS. 4-8 so those will not be described in detail.

Figures 9A, 9B:
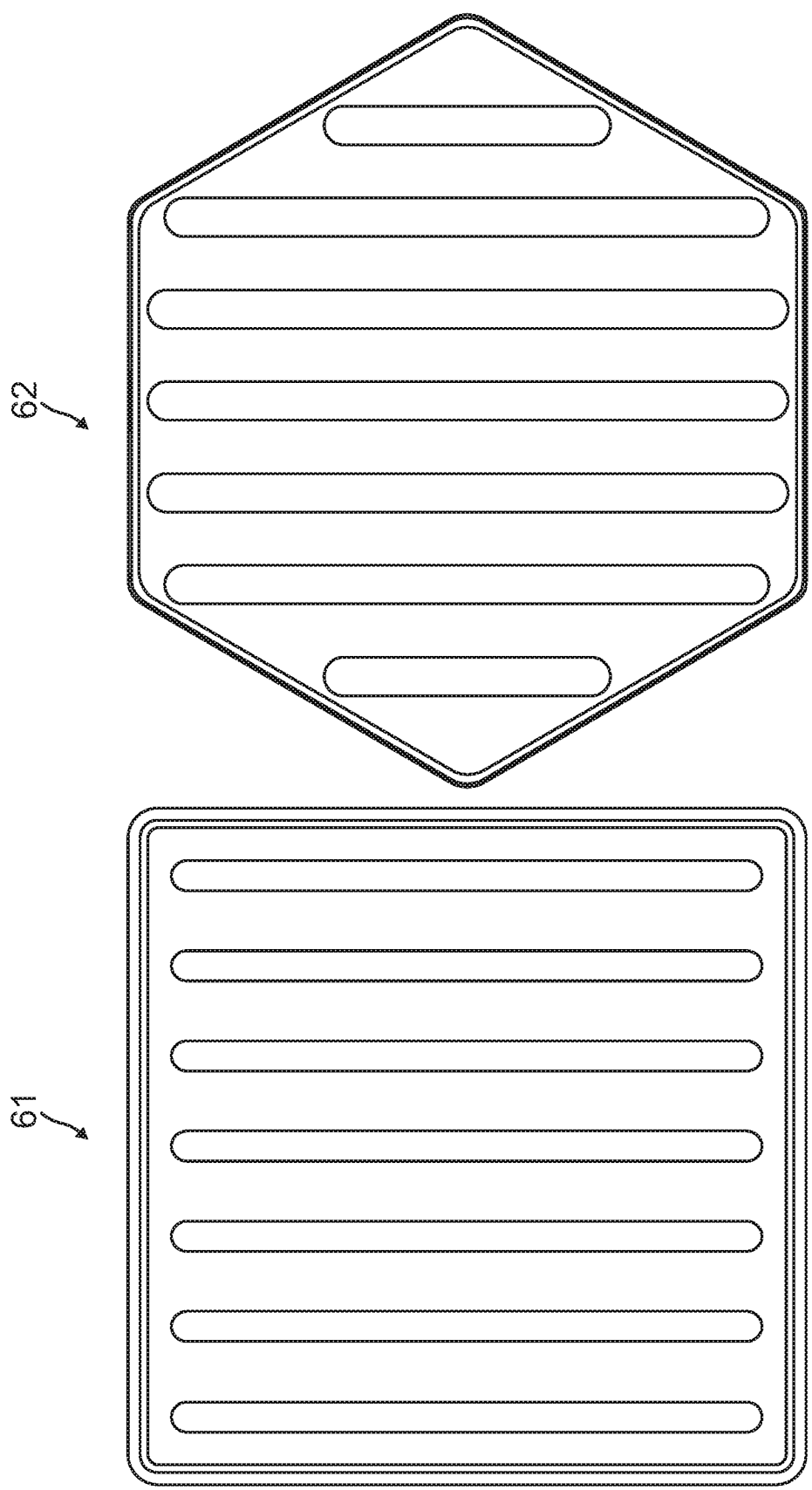
FIGS. 9A-9E are plan views of embodiments of the device similar to FIGS. 4-6 and having alternative shapes.
Figure 9C:
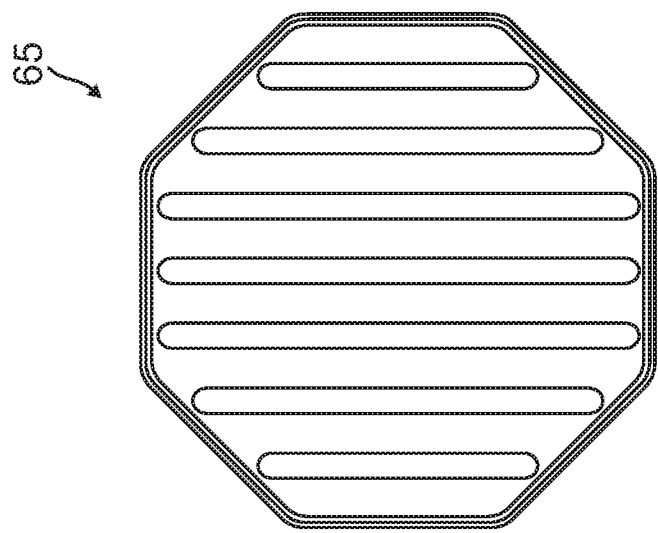
Figure 9D:
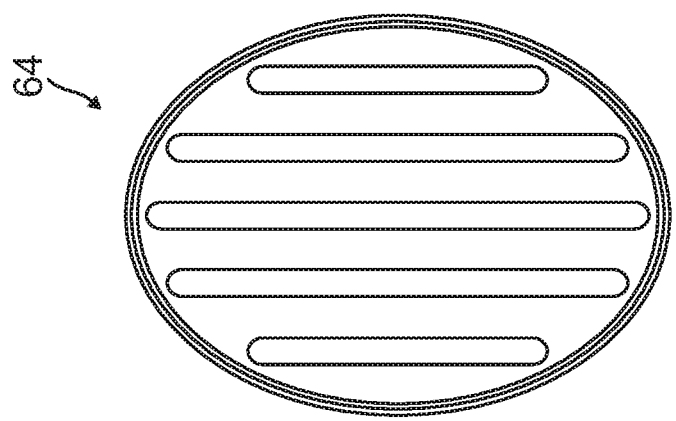
Figure 9E:
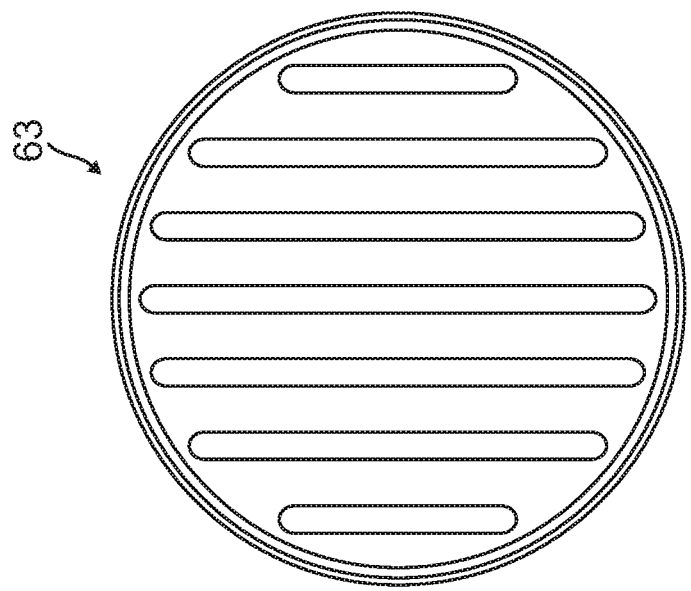
Figure 10:
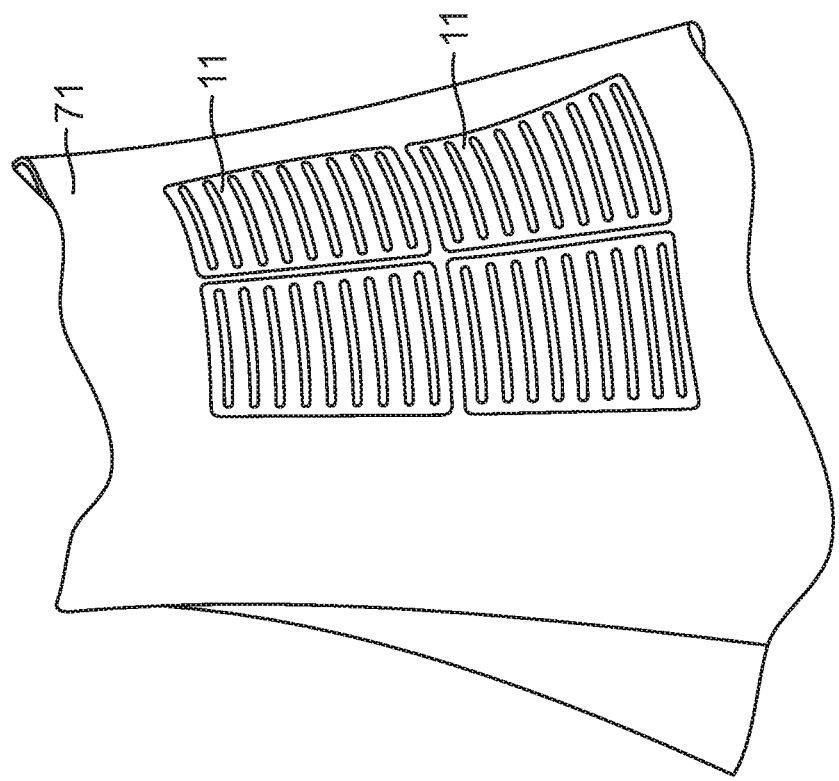
FIG. 10 is a partial perspective view of a segment of the back of a hood with a group of four of the devices of FIG. 4 mounted therein.

In FIG. 9A, device 61 is square, device 62 in FIG. 9B is hexagonal, device 63 in FIG. 9C is circular, device 64 in FIG. 9D is oval, and device 65 in FIG. 9E is octagonal. There may well be other possible or suitable shapes and those shown in the drawing are examples only.

Figure 11A:
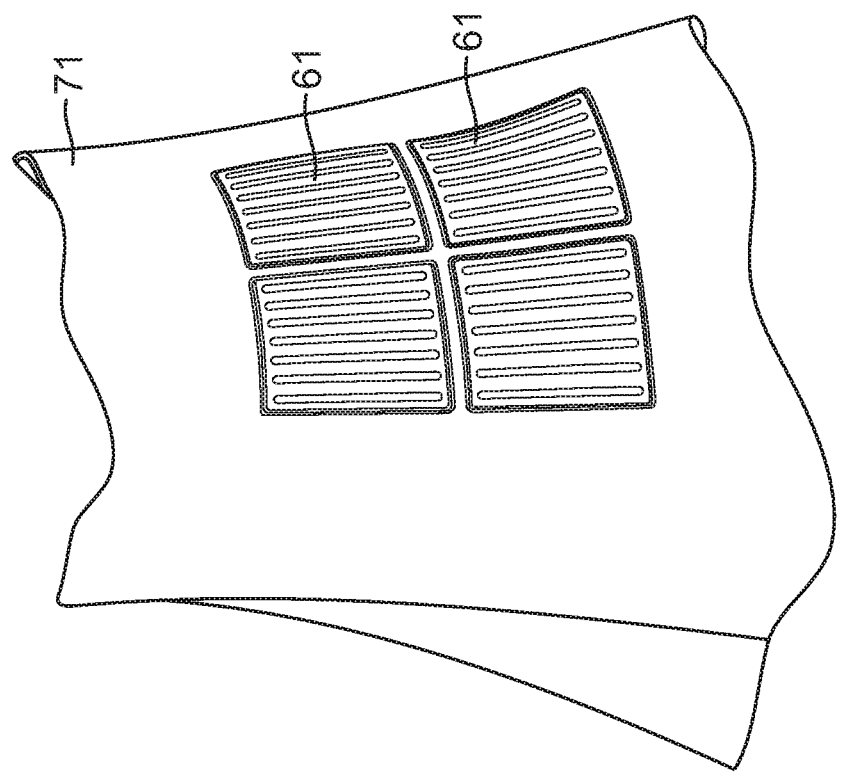
FIGS. 11A-11E are partial perspective views similar to FIG. 10 showing groupings of the devices of FIG. 9 mounted in the fabric of a hood.
Figure 11C:
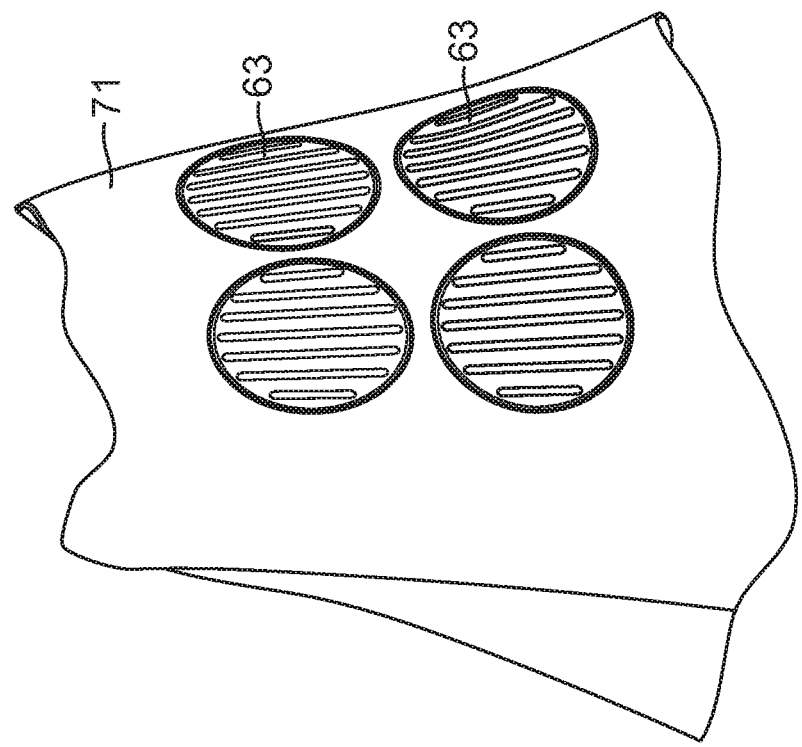
Figure 11B:
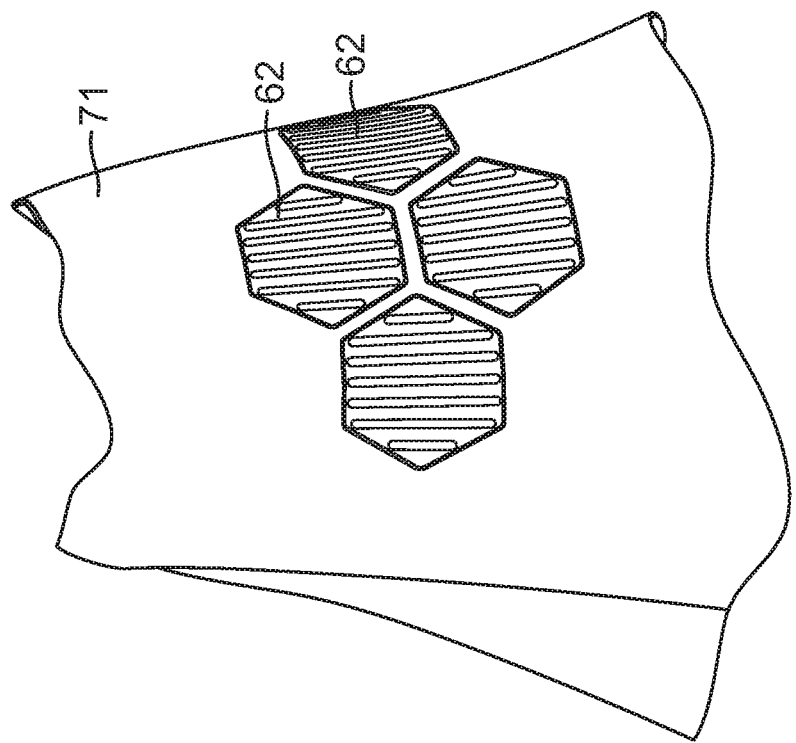
Figure 11E:
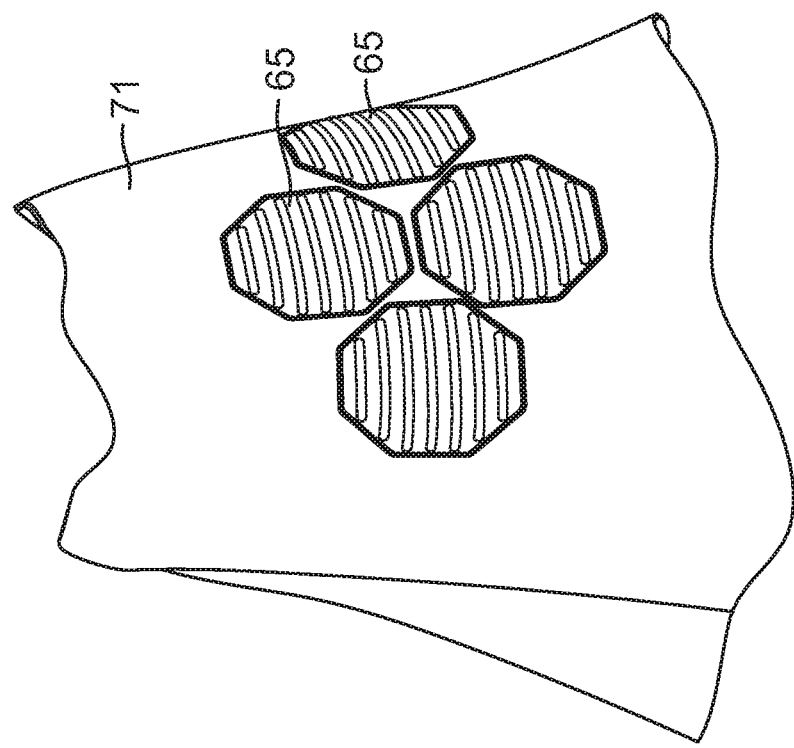
Figure 11D:
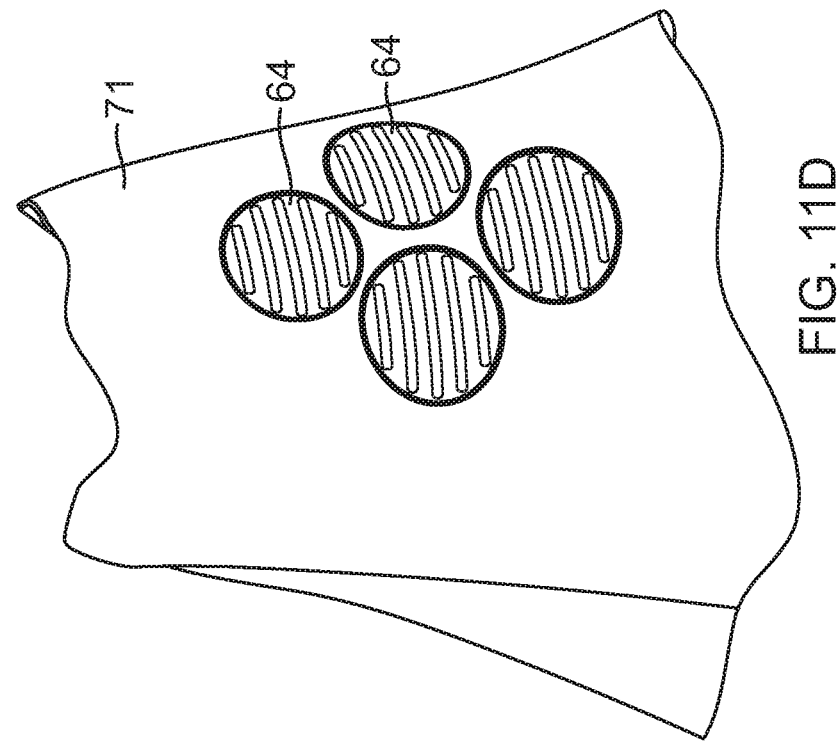

Some alternative hood device arrangements are shown in FIGS. 10 and 11A-E. Hood segments 71 are employed in each figure with different radiation shield device installations. For explanatory purposes, in FIG. 10 the hood segment is fitted with tour devices 11. Depending upon the requirements of the purchaser, the number of ventilation devices could be as few as one to as many as size permits and requirements dictate. The four rectangular devices 11 are arranged as shown. In this case the slots are oriented horizontally, but they could be oriented vertically as well, as are devices 61 mounted to hood 71 in a square group of square devices in FIG. 11A. A group of four hexagonal devices 62 are shown in FIG. 11B, a group of four circular devices 63 are mounted in hood 71 in FIG. 11C, four oval devices 64 are shown in FIG. 11D, and four octagonal devices 65 are shown in FIG. 11E.

The manner of attachment, and some variations in the schematic partial cross-sectional representations of devices 11 as they may be mounted to hood 71 are shown in FIGS. 2A-E.

Figure 12E:
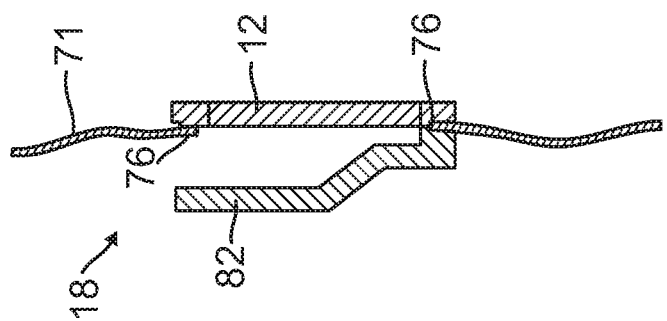
FIGS. 12D-12E show alternative embodiments of the devices of the prior figures as mounted in different ways in openings in a hood fabric.
Figure 12D:
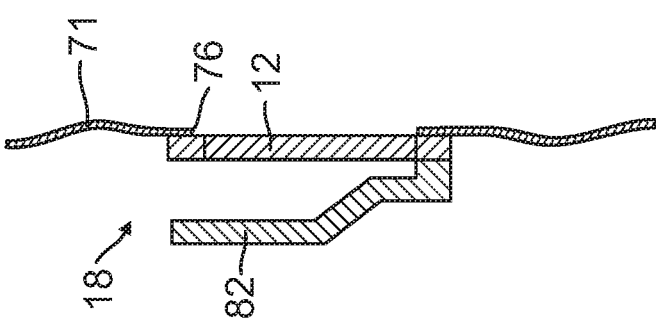
Figure 12C:
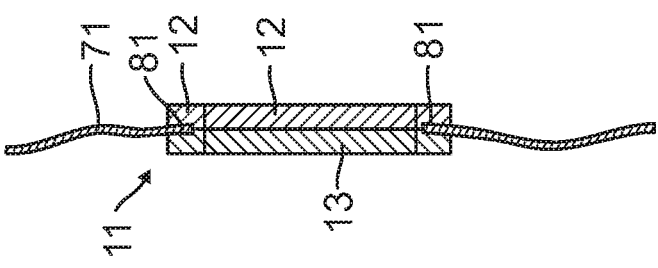
FIGS. 12A-12C are schematic partial sectional views of the type of FIG. 3A showing alternative mountings of embodiments of the devices of the prior figures as they can be secured in openings in a hood fabric.
Figure 12B:
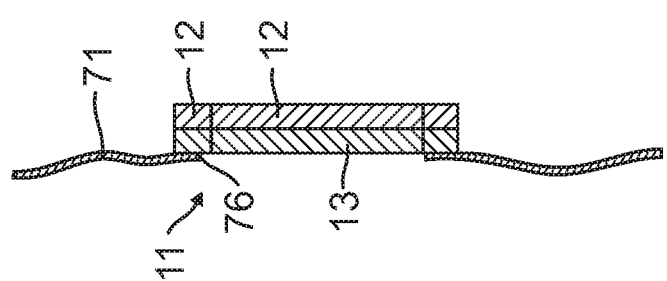
Figure 12A:
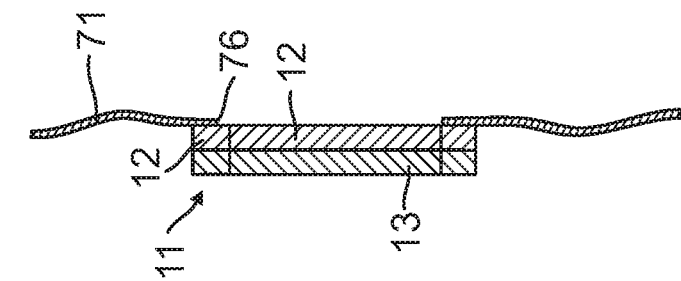

FIG. 12A represents the mounting arrangement of FIG. 3, where device 11 is mounted on the inside of the fabric of hood 71. Alternatively, device 11 can be mounted over opening 76 on the outside of the hood fabric, as shown in FIG. 12B.

An alternative is shown in FIG. 12C, where device 11 is formed with a peripheral groove or slot 81 at the intersection of plates 12 and 13 so that the edges of opening 76 in the hood fabric are positioned within that slot and the stitches are applied in the same way as before, through the hood fabric and through plates 12 and 13 in groove 45.

As another alternative mounting method, hood 71 can be two-ply and device 11 may be sandwiched between the hood fabric sheets, somewhat as a combination of FIGS. 12A and 12B.

In FIGS. 12D and 12E radiation shield device 18 has the usual first plate 12 and a modified inside element 82 instead of flat second plate 13. The same criteria apply as before, that is, that there is no direct path through the slots in plate 12 that can get past element 82 so any arc-flash energy cannot get through hood 71. An energy that enters through the slots in plate 12 is blocked by element 82. With this configuration element 82 does not have any slots at all because air flows through the space between plate 12 and element 82. Any arc-flash energy that impinges upon front plate 12 is partially blocked and absorbed by plate 12, and any such energy that passes through the slots in plate 12 is, blocked, absorbed, and deflected by baffle plate 82. Even though there are no slots in plate 82, the air flow through plate 12 to plate 82 is still in a semi-tortuous path.

Plate 12 in FIG. 12D is mounted in opening 76 in hood 71 in the same matter as shown in FIG. 12A. Plates 12 and 82 in FIG. 12E are mounted to hood 71 as shown in FIG. 12B at the top and as shown in FIG. 12C at the bottom where edge 76 of the hood opening is in a groove at the intersection of the two plates.

The alternative configurations and mounting arrangements of FIG. 12 are provided to show that there may be many ways that the radiation shield device may be mounted in an opening 76 in the fabric of hood 71, and these are merely examples to suggest that there may be many more. Radiation shield 11, 18 effectively blocks arc-flash energy while, at the same time, allowing fluid flow therethrough for both safety and comfort of the wearer.

What is claimed is:

1. A blackbody radiation shield device for use with a personal protection assembly incorporating a face shield, the device comprising:

a hood configured to cover at least the head of a wearer and incorporating the personal protection assembly, the hood and face shield being formed of materials that act as a blackbody radiation shield and protect the wearer from arc-flashes, said hood having an opening in at least one location;

a passive fluid flow blackbody radiation shield device mounted in said opening, said passive fluid flow blackbody radiation shield device having a periphery, said hood being secured to the periphery of said passive fluid flow blackbody radiation shield device, said passive fluid flow blackbody radiation shield device comprising:

a relatively rigid first plate having a first plurality of slots therethrough; and a relatively rigid second plate having a second plurality of slots therethrough;

said first and second plates being arranged in face-to-face relationship with said slots in said first and second plates, the slots being in offset registration so that there is no direct fluid flow route through the slots in said first and second plates, the first and second plates formed as two coplanar segments, the first plate formed with a peripheral rim thicker than a central portion of said first plate, which central portion faces said second plate, and which peripheral rim is formed with a peripheral groove, said central portion of said first plate is formed with a plurality of stand-offs which are in the plane of said peripheral rim, the path through the slots thereby providing a semi-tortuous path for fluid flow between internal and external sides of said hood;

said fluid flow blackbody radiation shield device being formed of materials that block arc-flashes, the semi-tortuous path thereby protecting the wearer from an external arc-flash while permitting fluid flow therethrough.

2. The device recited in claim 1, wherein said first plurality of slots in said first plate differs in number from said second plurality of slots in said second plate.

3. The device recited in claim 1, wherein said first plurality of slots in said first plate is equal in number to said second plurality of slots in said second plate.

4. The device recited in claim 1, wherein said first plurality of slots defines a first plurality of lands therebetween, and said second plurality of slots defines a second plurality of lands therebetween.

5. The device recited in claim 1, wherein said first plurality of slots defines a first plurality of lands therebetween, and said second plurality of slots defines a second plurality of lands therebetween and wherein said plurality of stand-offs are formed on said first plurality of lands to maintain spacing between the facing surfaces of said first and second plates.

6. The device recited in claim 1, wherein said first plate is formed with a peripheral groove in the surface facing away from said second plate.

7. The device recited in claim 6, wherein said passive fluid flow blackbody radiation shield device is mounted in said opening by stitches through said peripheral groove in said first plate, through said second plate, and through the hood material.

* * * * *